United States Patent
Friess et al.

(12)

(10) Patent No.: US 6,258,374 B1
(45) Date of Patent: Jul. 10, 2001

(54) FOAM-FORMING PHARMACEUTICAL COMPOSITION

(75) Inventors: Stefan Friess; Harald Heckenmüller; Heike Kublik; Oliver Szambien, all of Wedel (DE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/155,250

(22) PCT Filed: Sep. 3, 1998

(86) PCT No.: PCT/SE98/01568

§ 371 Date: Sep. 24, 1998

§ 102(e) Date: Sep. 24, 1998

(87) PCT Pub. No.: WO99/12521

PCT Pub. Date: Mar. 18, 1999

(30) Foreign Application Priority Data

Sep. 8, 1997 (SE) ................................... 9703226

(51) Int. Cl.⁷ ................ A61F 9/02; A61F 6/06; A61F 13/02
(52) U.S. Cl. ............... 424/436; 424/430; 424/431
(58) Field of Search .................... 424/430, 433, 424/436

(56) References Cited

U.S. PATENT DOCUMENTS

| 4,599,082 | * | 7/1986 | Grimard ............... 604/90 |
| 4,613,326 | * | 9/1986 | Szwarc ................ 604/89 |
| 4,929,230 | * | 5/1990 | Pfleger ............... 604/90 |
| 5,089,606 |   | 2/1992 | Cole et al. . |

FOREIGN PATENT DOCUMENTS

| 0 153 836 A2 |   | 4/1985 | (EP) . |
| 0340880A2 | * | 11/1986 | (EP) . |

* cited by examiner

*Primary Examiner*—Carlos A. Azpuru
(74) *Attorney, Agent, or Firm*—Fish & Richardson P.C.

(57) ABSTRACT

The invention provides a pharmaceutical composition for rectal or vaginal administration which comprises at least two parts wherein the composition comprises (i) two or more physiologically acceptable substances each in separate parts of the composition which are such that on admixture they react to produce a physiologically acceptable gas;

(ii) in at least one part of the composition a polymer stabiliser which is adapted to facilitate the formation of a water-soluble collapsible foam structure; and (iii) in at least one part of the composition a pharmaceutically active substance; an its use in the treatment or prophylaxis of disorders of the intestines, rectum or vagina.

25 Claims, No Drawings

FOAM-FORMING PHARMACEUTICAL COMPOSITION

This application is a 371 of PCT/SE98/01568 filed Sep. 3, 1998.

FIELD OF THE INVENTION

The present invention provides a pharmaceutical composition for rectal or vaginal administration and its use in therapy.

BACKGROUND OF THE INVENTION

Various means of administering drugs to the intestine are known. For example oral controlled release compositions are used to reach the upper part whereas enemas are used to reach the lower part. Enemas are usually used in the form of a foam to overcome the problem of leakage from the rectum following administration which makes it necessary for patients to lie down during administration. Foams, as well as pessaries, tampons and creams are used to administer drugs to the vagina.

Conventional foams for rectal or vaginal administration are filled in pressurised containers with a pharmaceutically active ingredient dissolved or suspended in a liquid vehicle, at least one propellant gas and a surfactant with foaming properties. Examples based on mesalazine, peppermint, sucralfate or budesonide as the active ingredient dispersed in a liquid vehicle containing a foaming surfactant and administered for topical action in the colon using a pressurised atomiser with a propellant gas are described in EP-A-468 555. Rectal foams formed by a propellant gas on expulsion from a pressurised container and containing other active ingredients such as flunisolide and its derivatives (see WO 94/12187), 5-aminosalicylic acid (EP 395 329), and 4-aminosalicylic acid (DE 4316724) have also been described.

Chlorofluorocarbons are generally used as the propellant gas but these are undesirable for environmental reasons. Also the use of pressurised containers to administer pharmaceutically active substances suffers from a number of problems. For example, it is difficult to administer an accurate dose of the pharmaceutical composition of the drug; the containers are difficult to store over long periods of time because of leakage of gas which results in reduced administration capacity. Furthermore the disposal of used containers can be dangerous because of the risk of explosions on incineration. Accordingly alternative formulations need to be found.

DESCRIPTION OF THE INVENTION

According to the invention there is provided a pharmaceutical composition for rectal or vaginal administration which comprises at least two parts wherein the composition comprises (i) two or more physiologically acceptable substances each in separate parts of the composition which are such that on admixture they react to produce a physiologically acceptable gas;

(ii) in at least one part of the composition a polymer stabiliser which is adapted to facilitate the formation of a water-soluble collapsible foam structure; and (iii) in at least one part of the composition a pharmaceutically active substance.

During administration the individual parts of the composition are mixed which causes the two or more substances defined in (i) to react to produce a gas which contacts the polymer stabiliser (ii) forming a water-soluble collapsible foam which may then be applied to the rectum or vagina. The polymer stabiliser is preferably used in a swelled form, e.g. in the form of a hydrogel. The composition of the invention is preferably administered from a multi-part syringe. The advantage of such a device is that the foaming action is smooth and the time for the administration is controllable using the piston of the syringe resulting in less discomfort for the patient.

The two or more substances defined in (i) are preferably one or more acids, especially water-soluble acids and one or more effervescent compounds. Each is generally used as an aqueous solution in a concentration of from 0.1 to 10% by weight of the compositions.

The acid is preferably hydrochloric acid or a water-soluble mono- or polycarboxylic acid. Examples of suitable water-soluble mono- or polycarboxylic acids include citric, lactic, tartaric, succinic, glycollic, malonic, oxalic, malic, flumaric, maleic, or acetic acid. Most preferred is citric acid, preferably in a concentration of from 1 to 3% by weight of the composition.

The effervescent compound is preferably a pharmaceutically acceptable alkali metal carbonate or bicarbonate e.g. sodium monohydrogen carbonate, potassium monohydrogen carbonate, sodium carbonate or potassium carbonate. Most preferred is sodium monohydrogen carbonate, preferably in a concentration of from 3.5 to 5.5% by weight of the composition. The exact concentration of each substance to be used depends on the volume of foam required and the desired pH and osmolarity of the foam to be formed. Generally where the two substances (i) are an acid and an effervescent compound, they should be used in a ratio of from 1:0.5 to 1:25, preferably from 1:1 to 1:4, by weight of the acid to the effervescent compound.

The polymer stabiliser (ii) is preferably a hydrogel thickener. The polymer stabiliser used in the invention preferably displays pseudoplastic flow characteristics when in solution. More preferably the polymer stabiliser used in the invention is a water soluble hydrogel thickening polymer, e.g. a natural polysaccharide, semi-synthetic polymer or a synthetic polymer, or a mixture thereof Examples of natural polysaccharides are agar, alginates, carrageenan, guar, arabic, tragacanth, pectins, dextran, gellan and xanthan gums. Suitable semi-synthetic polymers are polysaccharide derivatives, e.g. cellulose esters and modified starches. Examples of synthetic polymers are polyvinyl alcohol, polyvinylpyrrolidone, polyacrylates, polyvinylacetate, and poloxamer. Preferably the viscosity of a solution thickened with the polymer stabiliser is remains substantially the same in a wide pH range and is relatively independent of ionic strength. More preferably the polymer stabiliser is xanthan gum or hydroxyethyl cellulose. Most preferably the polymer stabiliser is xanthan gum.

The advantage of xanthan gum is that compositions containing it have a low viscosity at high shear rates, therefore they are easy to pump, spray and spread. They exhibit a high viscosity at low shear rates. This results in a good stabilisation of suspended drugs.

The polymer stabiliser is preferably used in such concentrations that solutions or dispersions containing it in swelled form have a viscosity as measured by Bohlin® rotational viscosimeter CSR-10a within the ranges shown in Table 1 at the given shear rates. The concentration of a given polymer stabiliser required to meet the viscosity requirements may easily be determined empirically by a person of skill in the art.

TABLE 1

| Shear Rate (s$^{-1}$) | Viscosity Range (mPas) | Preferred Viscosity Range (mPas) |
|---|---|---|
| 0.1 | $10^1$–$10^{10}$ | $10^3$–$10^7$ |
| 1 | $10^1$–$10^9$ | $10^2$–$10^5$ |
| 10 | $10^1$–$10^8$ | $10^2$–$10^4$ |
| 100 | $10^1$–$10^5$ | $10^2$–$10^3$ |

In general the concentration of the polymer stabiliser should be from 0.1 to 5% by weight of the composition where it is xanthan gum or hydroxyethyl cellulose. Preferably the concentration of xanthan gum used is from 0.5 to 2% by weight of the composition and the concentration of hydroxyethyl cellulose where it is hydroxyethyl cellulose 4000 is from 2 to 3% by weight of the composition. When the polymer stabiliser is PVP 90, it is preferably used in a concentration of from 5 to 30% by weight of the composition, preferably 10 to 25% by weight.

The pharmaceutically active substance to be used in the present invention depends on the disease to be treated by the composition or intended effect of the composition. It is preferably one or more of an anti-inflammatory drug, analgesic, local anaesthetic, anti-infection drugs, contraceptive and/or an anti-anginal agent. Suitable anti-inflammatoy drugs include steroids or non steroidal anti-inflammatory drugs (NSAIDs). Preferred analgesics and local anaesthetics are lidocaine, morphine or codeine. Preferred steroids are budesonide, suitable esters of beclomethasone, rofleponide or suitable derivatives (e.g. esters) thereof, hydrocortisone, betamethasone, prednisolone, dexamethasone, fluocinolone, amcinonide, bufexamac or flunisolide. Particularly preferred is budesonide. Preferred NSAIDs are 4-aminosalicylic acid, 5-aminosalicylic acid or sulphasalazine. Preferred anti-infection drugs are anti-microbial agents (e.g. bacitracin or iodine), antiseptics (e.g. cetrimide), fungicides (e.g. clotrimazole, metronidazole or cyclospoline) and anti-viral agents (e.g. acyclovir or idoxuridin). Preferred anti-anginal agents are isosorbide-5-mononitrate or isosorbide dinitrate. The pharmaceutically active substances can be administered alone or in combination.

The concentration of the pharmaceutically active substance to be used depends upon the intended volume of the foam to be produced by the composition on administration, the potency of the substance, the nature of the condition to be treated etc. and can easily be determined by a person of skill in the art.

The pH of the part of the composition comprising the pharmaceutically active substance and the pH of the foam resulting from mixing the two components depends upon the requirements for the stability of the pharmaceutically active substance incorporated therein. For example, when the pharmaceutically active substance is budesonide, the pH of the part containing it should be from 2 to 5. At the time of administration of the composition of the invention, the pH of the foam should be from 5 to 8, which is a physiologically well tolerated pH range.

If the pharmaceutically active substance used in the present invention is suspended within one of the parts of the composition, it is preferably in micronised form. Preferably it has a particle size of below 20 μm in order to minimise the risk of sedimentation during storage of the composition and to facilitate the dispersion of the substance in the composition without decreasing the foam rigidity during administration.

The composition according to the invention may optionally comprise pharmaceutically acceptable excipients such as surfactants, preservatives, and other types of stabilisers, for example antioxidants, chelating agents, tonicity modifiers (e.g. sodium chloride, mannitol, sorbitol or glucose), spreading agents and water soluble lubricants, e.g. propylene glycol, glycerol or polyethylene glycol. The concentration of each excipient required may easily be determined empirically by a person skilled in the art.

Suitable surfactants include ionic surfactants, e.g. lauryl sulphate, or non-ionic surfactants e.g. phospholipids, poloxamer, and polysorbate. Non-ionic surfactants are preferably used.

Suitable preservatives include benzalkonium chloride, parabens, chlorhexidine acetate, chlorhexidine gluconate, sorbic acid, potassium sorbitol, chlorbutanol and phenoxyethanol.

In order to improve the stability of the pharmaceutically active substance chelating agents such as EDTA or phosphates can be added.

Suitable spreading agents are those used for topical applications e.g. di-n-octyl ether (for example Cetiol® OE), fatty alcohol polyalkylene glycol ether (for example Aethoxal® B), 2-ethylhexyl palmitate (for example Cegesoft® C 24), and isopropyl fatty acid esters. The spreading agent should preferably be dispersed in the same part as the polymer stabiliser.

One advantage of using the composition of the invention is that since the gas used to form the foam is produced by reaction, the composition is under less pressure on administration which minimises the risk of inducing a defecation reaction reflex.

The composition according to the invention is such that it forms a foam which is collapsible. The volume of the foam formed by the composition preferably is reduced by 50% in from 2 to 120 minutes after administration and completely collapses to its original volume after 5 to 240 minutes. The time before the foam collapses is preferably sufficiently long so that the foam spreads as far up the colon as possible but it is preferably not so long that it is removed from the area to be treated by the natural movement of the intestines before it has collapsed.

The collapse time depends on a number of factors. For example the greater the amount of gas produced by the two or more substances (i) or the higher the viscosity of the component comprising the polymer stabiliser, the longer the collapse time. The collapse time also depends on the nature of the other additives to the composition which have surface active properties e.g. surfactants or preservatives.

The advantage of the collapsibility of the foam formed by the composition of the present invention is that removal of foam from the patient is more comfortable for the patient and there is less chance of the active substance being trapped in the centre of the foam ancL being unable to contact the area of the body to be treated.

The foam formed by the composition according to the invention is water-soluble because the composition is substantially free from water-insoluble di- or trivalent metal salts which could complex with the polymer stabiliser to make the foam insoluble.

The invention further provides the use of the composition according to the invention in the manufacture of a medicament for the treatment of disorders of the intestines, rectum or vagina. The invention also provides a method of treatment or prophylaxis of disorders of the intestines, rectum or vagina which comprises administering a therapeutically effective amount of the composition according to the invention to a patient suffering from or liable to suffer from a said disorder.

The present invention is further illustrated by the following examples which should not be interpreted as limiting the scope of the invention.

EXAMPLE 1

A composition according to the invention comprising the components set out in Table 2 was prepared. It was then mixed to form a foam whose collapsibility was determined.

Component 1 was prepared by dissolving the citric acid, sodium edetate and poloxamer in purified water and dispersing xanthan and budesonide in the resulting solution. To hydrate the xanthan the dispersion was agitated at room temperature under vacuum for 30 minutes. The resulting hydrogel was filled into one chamber of a two chamber mixing syringe s (MIXPAC System 50 manufactured by Mixpac Systems AG, Switzerland).

Component 2 was prepared by dissolving the sodium bicarbonate and sodium edetate in purified water and dispersing xanthan in the solution obtained by agitation at room temperature under vacuum for 30 minutes. The resulting alkaline hydrogel was filled in the other chamber of the two chamber syringe.

Both chambers of the syringe were connected with a mixing tip, in which thorough mixing of the two components took place upon discharging the chambers by a plunger.

The foam produced was filled into a measuring cylinder. The volume of the expanded foam was measured and its collapse with time was monitored.

10 g of each component was used and it took 10 seconds to discharge the syringe. A volume of 95 ml was obtained 5 seconds after discharge. After 5 minutes the volume had decreased to 90 ml, and after 10 minutes the volume had decreased to 85 ml. It took two and half hours before the foam collapsed completely. The pH of the foam was 6.28.

TABLE 2

| Ingredient | Component 1/g | Component 2/g |
| --- | --- | --- |
| Purified water | 10 | 10 |
| Citric acid | 0.28 | |
| Sodium monohydrogencarbonate | | 0.42 |
| Xanthan* | 0.1 | 0.1 |
| Sodium edetate | 0.001 | 0.001 |
| Poloxamer** | 0.02 | 0.02 |
| Budesonide | 0.002 | |

*Keltrol ® RD, Kelco, Hamburg
**Lutrol ® F68

EXAMPLE 2

A composition according to the invention comprising the components set out in Table 3 was prepared. It was then mixed to form a foam whose collapsibility was determined.

Component 1 was prepared by dissolving the citric acid, sodium edetate, polysorbate 80 and lidocain in purified water and dispersing hydroxyethyl cellulose in the solution obtained. The dispersion was agitated under vacuum at room temperature for 3 hours. The resulting hydrogel was filled into one chamber of a two chamber mixing syringe as used in Example 1.

Component 2 was prepared by dissolving sodium bicarbonate in purified water and dispersing hydroxyethyl cellulose in the solution obtained by agitation at room temperature and vacuum for 3 hours. A foam was generated as described in Example 1.

The foam produced was filled into a measuring cylinder. The volume of the expanded foam was measured and its collapse with time was monitored.

10 g of each component was used and it took 5 seconds to discharge the syringe. A volume of 86 ml was obtained 60 seconds after discharge. After 15 minutes the volume had decreased to 83 ml and after 30 minutes the volume had decreased to 69 ml. It took two hours before the foam collapsed completely. The pH of the foam was 6.82.

TABLE 3

| Ingredient | Component 1/g | Component 2/g |
| --- | --- | --- |
| Purified water | 10 | 10 |
| Citric acid | 0.28 | |
| Sodium monohydrogencarbonate | | 0.42 |
| Hydroxyethyl cellulose* | 0.28 | 0.28 |
| Surfactant** | 0.02 | 0.02 |
| Lidocain HCl | 0.2 | |

*Tylose H 4000 PHA
**Polysorbate 80

What is claimed is:

1. A pharmaceutical composition for rectal or vaginal administration which comprises at least two parts wherein the composition comprises
    (i) two or more physiologically acceptable substances each in separate parts of the composition which are such that on admixture they react to produce a physiologically acceptable gas;
    (ii) in at least one part of the composition a polymer stabiliser which is adapted to facilitate the formation of a water-soluble collapsible foam structure; and
    (iii) in at least one part of the composition a pharmaceutically active substance.

2. A composition according to claim 1 wherein the two or more substances defined in (i) are one or more acids and one or more effervescent compounds.

3. A composition according to claim 2 wherein the acid is a water-soluble acid.

4. A composition according to claim 1, wherein the polymer stabiliser is a hydrogel thickener.

5. A composition according to claim 1 wherein the pharmaceutically active substance is one or more of an anti-inflammatory drug, analgesic, local anaesthetic, anti-infection drug, contraceptive or vaso-active drug.

6. A method of treatment or prophylaxis of a disorder of the intestines, rectum or vagina which comprises administering a therapeutically effective amount of a composition according to claim 1 to a patient suffering from or liable to suffer from said disorder.

7. A composition according to claim 2, wherein the polymer stabiliser is a hydrogel thickener.

8. A composition according to claim 3, wherein the polymer stabiliser is a hydrogel thickener.

9. A composition according to claim 2, wherein the pharmaceutically active substance is one or more of an anti-inflammatory drug, analgesic, local anaesthetic, anti-infection drug, contraceptive or vaso-active drug.

10. A composition according to claim 3, wherein the pharmaceutically active substance is one or more of an anti-inflammatory drug, analgesic, local anaesthetic, anti-infection drug, contraceptive or vaso-active drug.

11. A method of treatment or prophylaxis of a disorder of the intestines, rectum or vagina which comprises administering a therapeutically effective amount of a composition according to claim 2 to a patient suffering from or liable to suffer from said disorder.

12. The method of claim 11, wherein the pharmaceutically active substance is one or more of an anti-inflammatory drug, analgesic, local anaesthetic, anti-infection drug, contraceptive or vaso-active drug.

13. The method of claim 11, wherein the two or more substances defined in (i) are one or more acids and one or more effervescent compounds.

14. The method of claim 13, wherein the acid is a water-soluble acid.

15. The method of claim 11, wherein the polymer stabiliser is a hydrogel thickener.

16. The composition of claim 5, wherein the pharmaceutically active substance is an anti-inflammatory drug selected from the group consisting of steroids and non-steroidal anti-inflammatory drugs.

17. The composition of claim 16, wherein the pharmaceutically active substance is a steroid selected from the group consisting of budesonide, esters of beclomethasone, rofleponide, esters of rofleponide, hydrocortisone, betamethasone, prednisolone, dexamethasone, fluocinolone, amcinonide, bufexamac, and flunisolide.

18. The composition of claim 16, wherein the pharmaceutically active substance is a non-steroidal anti-inflammatory drug selected from the group consisting of 4-aminosalicylic acid, 5-aminosalicylic acid, and sulphasalazine.

19. The composition of claim 5, wherein the pharmaceutically active substance is an analgesic selected from the group consisting of lidocaine, morphine, and codeine.

20. The composition of claim 5, wherein the pharmaceutically active substance is an anti-infection drug is an anti-microbial agent, antiseptic, fungicide, or antiviral agent.

21. The composition of claim 20, wherein the pharmaceutically active substance is selected from the group consisting of bacitracine, iodine, cetrimide, clotrimazole, metonidazole, cyclosporine, acyclovir, and idoxuridin.

22. The composition of claim 5, wherein the vaso-active drug is isosorbicle-5-mononitrate or isosorbide dinitrate.

23. A method of administering a pharmaceutical composition to the rectum or vagina, comprising:
(a) providing a multi-chamber syringe containing the pharmaceutical composition, the composition comprising two or more parts, each part containing a physiologically acceptable substance, the substances being selected so that on admixture they react to produce a physiologically acceptable gas, at least one part of the composition including a polymer stabilizer that is adapted to facilitate the formation of a water-soluble collapsible foam structure, and at least one part of the composition including a pharmaceutically active substance, each of the parts being disposed in a separate chamber of the syringe;
(b) delivering the parts of the composition from the chambers of the syringe to the rectum or vagina.

24. The method of claim 23 wherein the parts of the composition are mixed during delivery.

25. The method of claim 23 wherein the parts react to form a water-soluble collapsible foam.

* * * * *